(12) United States Patent
Luo et al.

(10) Patent No.: US 12,702,343 B2
(45) Date of Patent: Aug. 11, 2026

(54) ELECTROCARDIOGRAM EVALUATION METHOD

(71) Applicant: NEC Corporation, Tokyo (JP)

(72) Inventors: Yuan Luo, Tokyo (JP); Mitsuru Noma, Tokyo (JP); Osamu Hisamatsu, Tokyo (JP); Akihiko Shibano, Tokyo (JP); Hiroaki Kataoka, Tokyo (JP); Kosuke Nishihara, Tokyo (JP); Masahiro Kubo, Tokyo (JP)

(73) Assignee: NEC CORPORATION, Tokyo (JP)

( * ) Notice: Subject to any disclaimer, the term of this patent is extended or adjusted under 35 U.S.C. 154(b) by 156 days.

(21) Appl. No.: 18/849,580

(22) PCT Filed: Mar. 29, 2022

(86) PCT No.: PCT/JP2022/015448

§ 371 (c)(1),
(2) Date: Sep. 23, 2024

(87) PCT Pub. No.: WO2023/187987

PCT Pub. Date: Oct. 5, 2023

(65) Prior Publication Data

US 2025/0213167 A1 Jul. 3, 2025

(51) Int. Cl.
*A61B 5/346* (2021.01)

(52) U.S. Cl.
CPC .................................... *A61B 5/346* (2021.01)

(58) Field of Classification Search
CPC . A61B 5/0006; A61B 5/02055; A61B 5/1112; A61B 5/346; A61B 5/7267; G16H 10/60; G16H 50/20
See application file for complete search history.

(56) References Cited

FOREIGN PATENT DOCUMENTS

| | | | |
|---|---|---|---|
| CN | 113208609 | A | 8/2021 |
| JP | H06-181892 | A | 7/1994 |
| JP | 2020-130772 | A | 8/2020 |
| KR | 10-2016-0064607 | A | 6/2016 |
| WO | 2021/019984 | A1 | 2/2021 |

OTHER PUBLICATIONS

International Search Report for PCT Application No. PCT/JP2022/015448, mailed on May 10, 2022.

JP Office Action for JP Application No. 2024-510790, mailed on Oct. 7, 2025 with English Translation.

*Primary Examiner* — Michael T Rozanski
(74) *Attorney, Agent, or Firm* — Sughrue Mion, PLLC

(57) ABSTRACT

An electrocardiogram evaluation apparatus of the present invention includes: an electrocardiogram acquiring unit that acquires electrocardiogram data measured from a person; a circumstance acquiring unit that acquires circumstance data representing a circumstance in which the electrocardiogram data has been measured; and an evaluating unit that evaluates the electrocardiogram data based on the circumstance data.

10 Claims, 6 Drawing Sheets

Fig.1

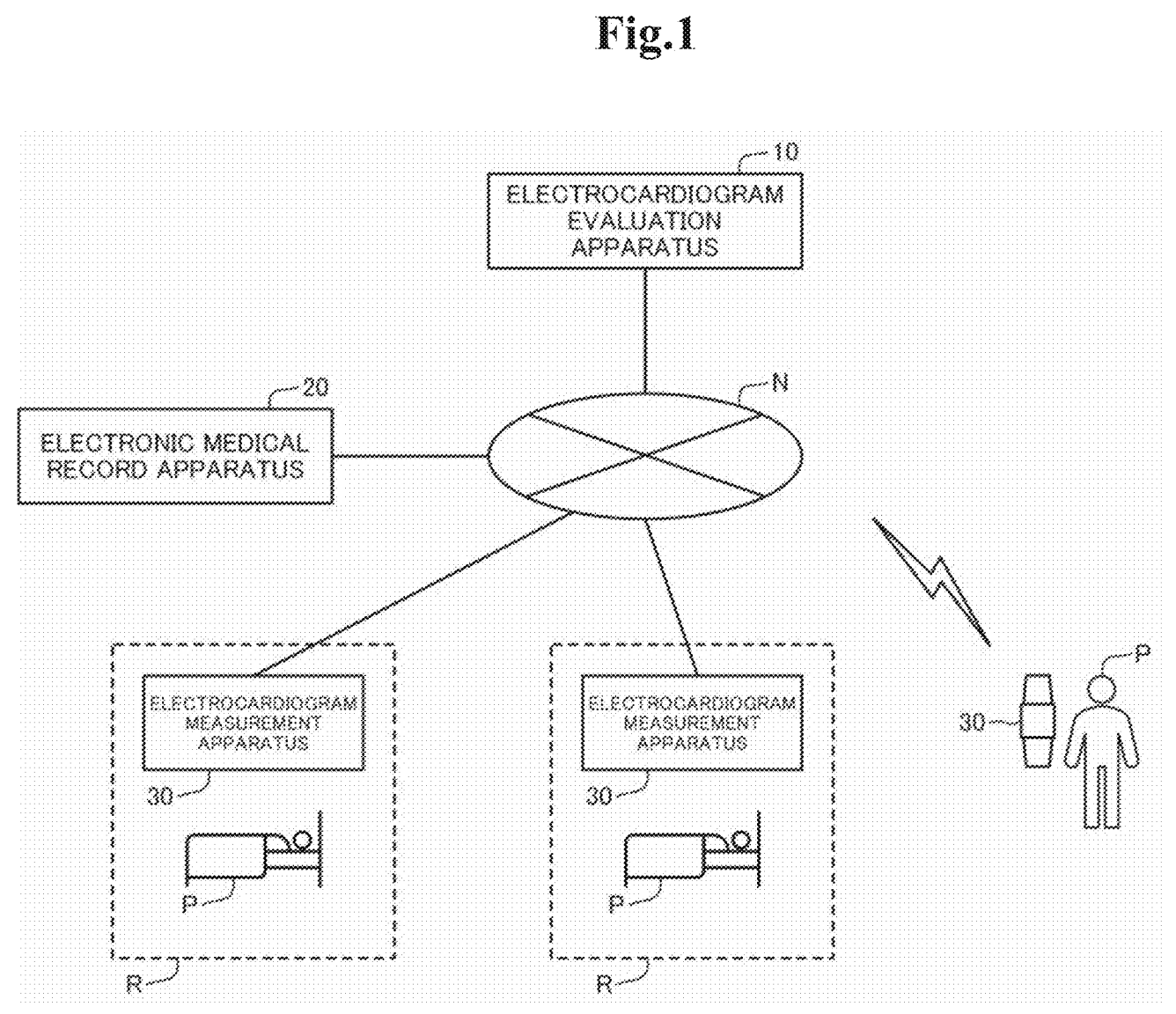

10
ELECTROCARDIOGRAM EVALUATION APPARATUS
N
20
ELECTRONIC MEDICAL RECORD APPARATUS
ELECTROCARDIOGRAM MEASUREMENT APPARATUS
30
P
R
ELECTROCARDIOGRAM MEASUREMENT APPARATUS
30
P
R
30
P

Fig.2

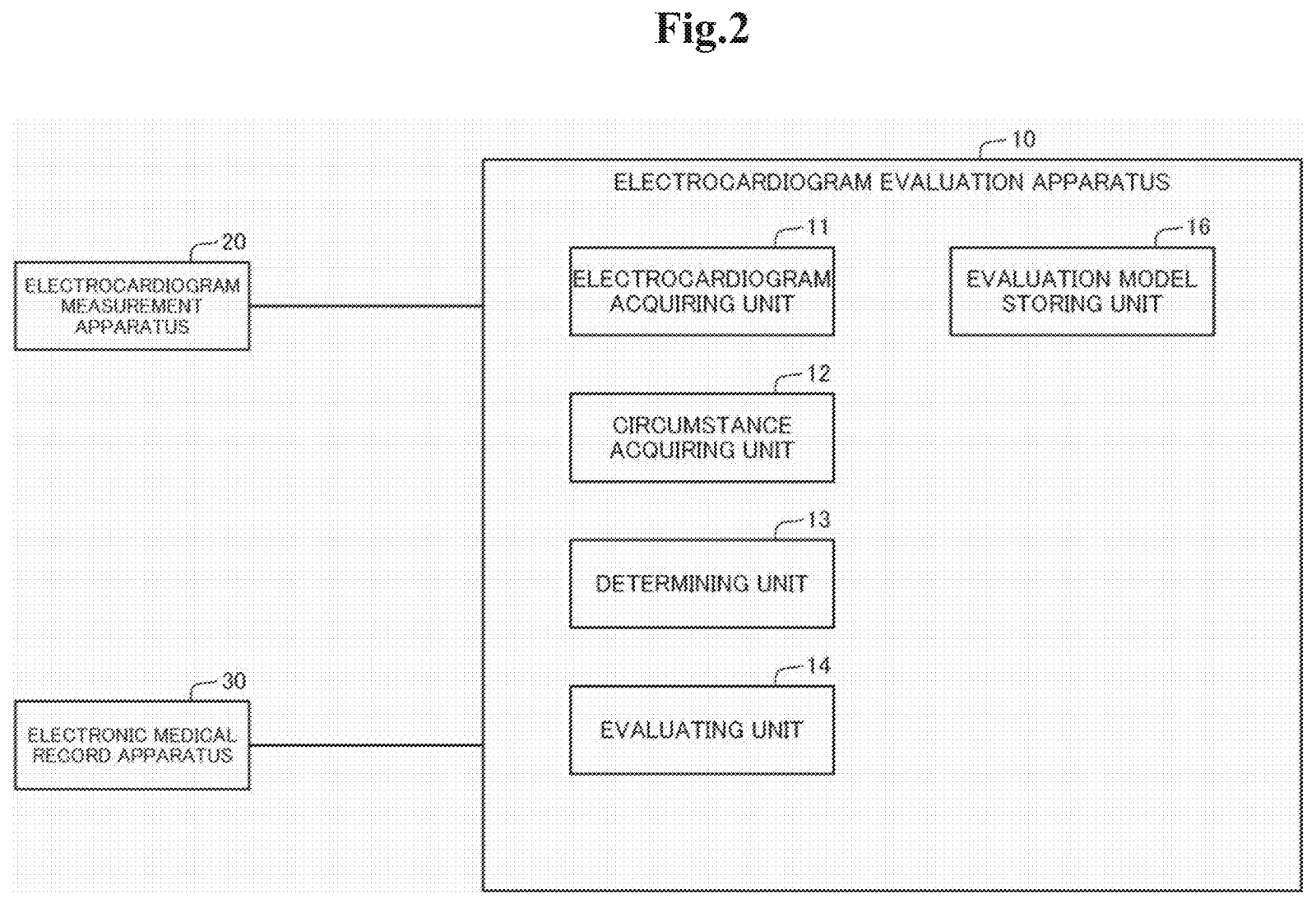

10 ELECTROCARDIOGRAM EVALUATION APPARATUS

11 ELECTROCARDIOGRAM ACQUIRING UNIT

12 CIRCUMSTANCE ACQUIRING UNIT

13 DETERMINING UNIT

14 EVALUATING UNIT

16 EVALUATION MODEL STORING UNIT

20 ELECTROCARDIOGRAM MEASUREMENT APPARATUS

30 ELECTRONIC MEDICAL RECORD APPARATUS

ELECTROCARDIOGRAM EVALUATION METHOD

This application is a National Stage Entry of PCT/JP2022/015448 filed on Mar. 29, 2022, the contents of all of which are incorporated herein by reference, in their entirety.

TECHNICAL FIELD

The present invention relates to an electrocardiogram evaluation method, an electrocardiogram evaluation apparatus, and a program.

BACKGROUND ART

One method for diagnosing a physical condition is to use an electrocardiogram. For example, in medical institutions, diagnosis of a physical condition is performed by measuring a 12-lead electrocardiogram with an electrocardiograph and evaluating the waveform of the electrocardiogram. Then, in recent years, as described in Patent Literature 1, an electrocardiogram is automatically analyzed and evaluated using a model generated through machine learning. For example, in Patent Literature 1, evaluation of an electrocardiogram is performed by generating a model by learning normal electrocardiograms and anomalous electrocardiograms of various diseases such as myocardial infarction, and inputting a measured electrocardiogram into the model.

CITATION LIST

Patent Literature

Patent literature 1: Japanese Unexamined Patent Application Publication No. JP-A 2020-130772

SUMMARY OF INVENTION

Technical Problem

However, even the electrocardiogram of a normal person may have a waveform similar to that of the electrocardiogram of a person with a disease. For example, the electrocardiograms of a healthy young person and a patient with acute myocardial infarction may have similar waveforms. Moreover, electrocardiograms with different diseases may have similar waveforms. For example, the waveforms of electrocardiograms may be similar between myocardial infarction and subarachnoid hemorrhage. Consequently, a problem arises that it is difficult to accurately evaluate an electrocardiogram.

An object of the present invention is to provide an electrocardiogram evaluation method which can solve the abovementioned problem that it is difficult to accurately evaluate an electrocardiogram.

Solution To Problem

An electrocardiogram evaluation method as an aspect of the present invention includes:

acquiring electrocardiogram data measured from a person;

acquiring circumstance data representing a circumstance in which the electrocardiogram data has been measured; and evaluating the electrocardiogram data based on the circumstance data.

Further, an electrocardiogram evaluation apparatus as an aspect of the present invention includes:

an electrocardiogram acquiring unit that acquires electrocardiogram data measured from a person;

a circumstance acquiring unit that acquires circumstance data representing a circumstance in which the electrocardiogram data has been measured; and an evaluating unit that evaluates the electrocardiogram data based on the circumstance data.

Further, a computer program as an aspect of the present invention includes instructions for causing a computer to execute processes to:

acquire electrocardiogram data measured from a person;

acquire circumstance data representing a circumstance in which the electrocardiogram data has been measured; and evaluate the electrocardiogram data based on the circumstance data.

Advantageous Effects Of Invention

Configured as described above, the present invention enables accurate evaluation of an electrocardiogram.

BRIEF DESCRIPTION OF DRAWINGS

FIG. 1 is a view showing the overall configuration of an information processing system in a first example embodiment of the present invention.

FIG. 2 is a block diagram showing the configuration of an electrocardiogram evaluation apparatus disclosed in FIG. 1.

DESCRIPTION OF EXAMPLE EMBODIMENTS

First Example Embodiment

Figure 3:
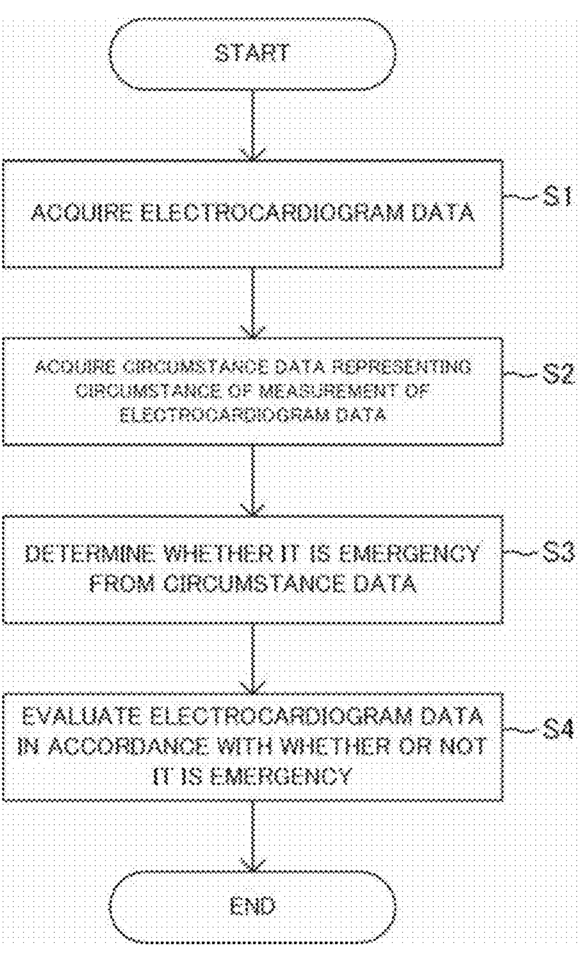
FIG. 3 is a flowchart showing the operation of the electrocardiogram evaluation apparatus disclosed in FIG. 1.

A first example embodiment of the present invention will be described with reference to FIGS. 1 to 3. FIGS. 1 and 2 are views for describing the configuration of an information processing system, and FIG. 3 is a view for describing the processing operation of the information processing system.

Configuration

The information processing system of the present invention is for evaluating an electrocardiogram in order to diagnose a physical condition of a person in a medical institution. For example, the information processing system is for evaluating a normal condition and an anomalous state such as myocardial infarction and subarachnoid hemorrhage from an electrocardiogram using a model generated through machine learning.

As shown in FIG. 1, the information processing system includes an electrocardiogram evaluation apparatus 10, an electronic medical record apparatus 20, and an electrocardiogram measurement apparatus 30, which are connected via a network N. The respective components will be described in detail below.

The electrocardiogram measurement apparatus 30 is an apparatus that measures an electrocardiogram from a person P. For example, the electrocardiogram measurement apparatus 30 is an electrocardiograph installed in a predetermined location R in a medical institution, such as a hospital room, an examination room, and an intensive care unit, or an electrocardiograph incorporated in a wearable device such as a wristwatch-type mobile terminal worn by a person P.

In addition to the configuration to measure an electrocardiogram, the electrocardiogram measurement apparatus 30 also includes a configuration included by a general information processing apparatus, such as a communication device and an arithmetic logic unit, and also includes a function to transmit measured electrocardiogram data to the electronic medical record apparatus 20. Consequently, electrocardiogram data measured by the electrocardiogram measurement apparatus 30 is stored in an electronic medical record for each person P. As an example, an operator of the electrocardiogram measurement apparatus 30 specifies an electronic medical record for a person P who is a measurement target from among electronic medical records stored in the electronic medical record apparatus 20, and records the measured electrocardiogram data of the person P into the electronic medical record. In addition, in a case where the electrocardiogram measurement apparatus 30 is a wearable device, electrocardiogram data is transmitted to the electronic medical record apparatus 20 together with the identification information of the person P, and the electrocardiogram data is recorded in an electronic medical record corresponding to the person P. However, electrocardiogram data may be recorded into an electronic medical record by any method.

Further, when recording electrocardiogram data into the electronic medical record apparatus 20, the electrocardiogram measurement apparatus 30 transmits identification information such as its own IP address to the electronic medical record apparatus 20 in association with the electrocardiogram data. That is to say, the electrocardiogram measurement apparatus 30 transmits electrocardiogram data in association with identification information indicating the sender of the electrocardiogram data. At this time, the identification information may be data that identifies a location where the electrocardiogram measurement apparatus 30 that is the sender of the electrocardiogram data is installed, that is, a location of measurement of the electrocardiogram. For example, by assigning different identification information to the respective electrocardiogram measurement apparatuses 30 installed in locations R such as a hospital room, an examination room and an intensive care unit, and storing correspondence information between the respective locations R and the respective identification information in the electronic medical record apparatus 20 or the electrocardiogram evaluation apparatus 10 to be described later, it is possible to identify a location of measurement of electrocardiogram data from the identification information associated with the electrocardiogram data. Also, in a case where the electrocardiogram measurement apparatus 30 is a wearable device, associating identification information such as an IP address or information indicating a wearable device with electrocardiogram data makes it possible to identify that the electrocardiogram data has been measured by the wearable device.

In addition, electrocardiogram data measured by the electrocardiogram measurement apparatus 30 may be directly transmitted to the electrocardiogram evaluation apparatus 10.

The electronic medical record apparatus 20 is configured with a general information processing apparatus including an arithmetic logic unit and a memory unit managed by a medical institution, and stores the electronic medical record of a person P in the memory unit. For example, the examination result and diagnosis result of the person P are recorded in the electronic medical record. As an example, the following data of the person P are recorded in the electronic medical record: basic physical data such as age, gender, height, and weight; measurement data such as heart rate, body temperature, blood pressure, and electrocardiogram data mentioned above; examination data such as blood test result and image diagnosis result; and medical condition data such as state of consciousness, current or past disease, condition at the time of diagnosis, and condition at the time of examination. Record data in the electronic medical record is recorded by input of data by a diagnostician or an examiner, or by transmission of data from the electrocardiogram measurement apparatus 30 such as an electrocardiogram a wearable device mentioned above or from various examination devices and measurement devices.

At this time, the electrocardiogram data to be recorded in the electronic medical record is stored in association with information identifying a location of measurement of the electrocardiogram, such as the abovementioned identification information. Moreover, the electrocardiogram data is stored in association with data that represents circumstances at the time of measurement, for example, the course of events of measurement of the electrocardiogram. As an example, the data representing the course of events of measurement of the electrocardiogram includes a measurement taken when the person P visits the medical institution as a patient in a general outpatient or emergency outpatient unit, a measurement taken while the person P is hospitalized in a general ward or intensive care unit, and a measurement taken routinely using a wearable device.

The electrocardiogram evaluation apparatus 10 is configured with one or a plurality of information processing apparatuses each including an arithmetic logic unit and a memory unit. Then, as shown in FIG. 2, the electrocardiogram evaluation apparatus 10 includes an electrocardiogram acquiring unit 11, a circumstance acquiring unit 12, a determining unit 13, and an evaluating unit 14. The respective functions of the electrocardiogram acquiring unit 11, the circumstance acquiring unit 12, the determining unit 13, and the evaluating unit 14 can be realized by the arithmetic logic unit executing a program for realizing the respective functions stored in the memory unit. In addition, the electrocardiogram evaluation apparatus 10 includes an evaluation model storing unit 16. The evaluation model storing unit 16 is configured with the memory unit. The respective components will be described in detail below.

At the time of diagnosis of a person P, the electrocardiogram acquiring unit 11 acquires electrocardiogram data of the corresponding person P from the electronic medical record apparatus 20 described above. However, the electrocardiogram acquiring unit 11 may automatically acquire electrocardiogram data at a preset timing such as at a fixed time interval. In addition, the electrocardiogram acquiring unit 11 may acquire electrocardiogram data from the electrocardiogram measurement apparatus 30.

At the time of diagnosis of the person P, the circumstance acquiring unit 12 acquires circumstance data representing a circumstance in which the electrocardiogram data acquired as described above has been measured from the person P. For example, the circumstance acquiring unit 12 acquires record data of the corresponding person P from the electronic medical record apparatus 20 as circumstance data. As an example, the circumstance acquiring unit 12 identifies the installation location of the electrocardiogram measurement apparatus 30 as a location where the electrocardiogram has been measured, from the identification information of the electrocardiogram measurement apparatus 30 that is data of the sender of the electrocardiogram data associated with the electrocardiogram data as described above, and acquires the location as circumstance data, and acquires the course of events of measurement of the electrocardiogram data associated with the electrocardiogram data as circumstance data. However, the circumstance acquiring unit 12 may automatically acquire circumstance data at a preset timing such as at a fixed time interval. In addition, the circumstance acquiring unit 12 may acquire the abovementioned circumstance data from data associated with the electrocardiogram data from the electrocardiogram measurement apparatus 30.

Further, the circumstance acquiring unit 12 also acquires any record data recorded in the electronic medical record of the person P. For example, the circumstance acquiring unit 12 also acquires basic physical data such as age, gender, height and weight, measurement data such as heart rate, body temperature and blood pressure, and medical condition data such as state of consciousness, current or past disease, condition at the time of diagnosis and condition at the time of examination, which are recorded in the electronic medical record of the person P.

The determining unit 13 determines the current physical condition of the person P based on the acquired circumstance data. For example, the determining unit 13 determines, as the physical condition of the person P, whether or not it is an emergency. Specifically, the determining unit 13 determines whether or not the physical condition of the person P is an emergency, for example, based on the course of events and location that the electrocardiogram data of the person P has been measured among the circumstance data acquired as described above. As an example, in the case of the course of events that the person P has been measured in an emergency outpatient unit or in the case of measurement in an intensive care unit, the determining unit 13 determines that it is an emergency. On the other hand, in the case of the course of events that the person P has been measured in a general outpatient unit or in the case of measurement with a wearable device, the determining unit 13 determines that it is not an emergency. In addition, the determining unit 13 may determine the degree of emergency set in stages based on the circumstance data.

Further, the determining unit 13 may determine the current physical condition of the person P based on the acquired record data of the person P. For example, the determining unit 13 may determine that the physical condition of the person P is an emergency based on the age, current and past medical histories and so forth of the person P. Moreover, the determining unit 13 may determine, as the physical condition of the person P, the attribute of the physical condition of the person P not only based on whether or not it is an emergency but also simply based on the current age and medical history. For example, the determining unit 13 may determine an advanced age, a chronic disease and so on as the attribute of the physical condition of the person P.

As described above, the evaluating unit 14 evaluates the electrocardiogram data based on the circumstance data representing the course of events and location that the electrocardiogram data has been measured from the person P and the record data on the body of the person P. Specifically, the evaluating unit 14 selects an evaluation model corresponding to the physical condition of the person P determined based on the circumstance data and the record data as described above, and evaluates the electrocardiogram data of the person P using the selected evaluation model. Here, the evaluation model is stored in the evaluation model storing unit 16, and is a model generated through learning of normal electrocardiograms and anomalous electrocardiograms of various diseases such as myocardial infarction. In particular, in this example embodiment, evaluation models corresponding to both a case where it is not an emergency and a case where it is an emergency are prepared through learning. As an example, by learning with a high weight on the electrocardiogram data of a person with a normal physical condition in a case where it is not an emergency and learning with a high weight on the electrocardiogram data of a person with an anomalous physical condition in a case where it is an emergency, the evaluation models according to the respective emergency levels are generated. Moreover, the evaluation models are prepared so as to correspond to the attributes of the person P determined as described above, such as an advanced age and a chronic disease. As an example, by learning with a high weight on the electrocardiogram data of a person of advanced age in the case of an attribute of an advanced age and learning with a high weight on the electrocardiogram data of a person suffering from a specific disease in the case of an attribute of a chronic disease, the evaluation models according to the respective emergency levels are generated.

The evaluating unit 14 inputs the electrocardiogram data of the target person P into the evaluation model selected in accordance with the determination result as described above, and performs evaluation based on output data that is output from the evaluation model. For example, as a result of inputting the electrocardiogram data into the evaluation model, when output data indicating a specific disease such as myocardial infarction is output, the evaluating unit 14 evaluates that there is a high possibility of the specific disease.

However, the evaluating unit 14 is not necessarily limited to evaluating electrocardiogram data using an evaluation model. For example, the evaluating unit 14 may extract a detection value that can be detected from the waveform of electrocardiogram data, compare the detection value with a preset reference value for evaluating electrocardiogram data, and evaluate the presence or absence of a specific disease from the result. At this time, the evaluating unit 14 may change a reference value to be compared with a value detected from electrocardiogram data in accordance with the abovementioned determination result, that is, whether or not it is an emergency and the attribute of a person P. As an example, reference values corresponding to whether or not it is an emergency and to the respective attributes of a person P may be set in advance, and a reference value according to the determination result may be selected from them and used to evaluate electrocardiogram data.

In addition, the evaluating unit 14 may calculate the physical anomaly degree of a person P, the emergency level of treatment for a person P, and the presence or absence of a specific disease as examples of the evaluation result of electrocardiogram data. However, the evaluating unit 14 may perform evaluation of any content as long as the content can be calculated from electrocardiogram data.

Operation

Next, the operation of the above electrocardiogram evaluation apparatus 10 will be described mainly with reference to a flowchart of FIG. 3.

First, at the time of diagnosis of a person P, the electrocardiogram evaluation apparatus 10 acquires electrocardiogram data of the person P (step S1). Next, the electrocardiogram evaluation apparatus 10 acquires circumstance data representing a circumstance in which the acquired electrocardiogram data has been measured from the person P (step S2). For example, the electrocardiogram evaluation apparatus 10 acquires data of a corresponding person P from the electronic medical record apparatus 20 as circumstance data. As an example, the electrocardiogram evaluation apparatus 10 acquires, from identification information of the electrocardiogram measurement apparatus 30 that is the sender of the electrocardiogram data associated with the electrocardiogram data as described above, the location of measurement of the electrocardiogram and the course of events of measurement of the electrocardiogram data associated with the electrocardiogram data. At this time, the electrocardiogram evaluation apparatus 10 may acquire any record data recorded in the electronic medical record of the person P.

Next, the electrocardiogram evaluation apparatus 10 determines the current physical condition of the person P based on the acquired circumstance data (step S3). Specifically, the electrocardiogram evaluation apparatus 10 determines whether or not it is an emergency as the physical condition of the person P. For example, the determining unit 13 determines that it is an emergency in the course of events that the person P has been measured in an emergency outpatient unit or in the case of measurement in a place such as an intensive care unit, and the determining unit 13 determines that it is not an emergency in the course of events that the person P has been measured in a general outpatient unit or in the case of measurement with a wearable device. At this time, the electrocardiogram evaluation apparatus 10 may determine the current physical condition of the person P based not only on the circumstance data but also on record data such as age and medical history of the person P.

Next, the electrocardiogram evaluation apparatus 10 evaluates the electrocardiogram data (step S4). At this time, the electrocardiogram evaluation apparatus 10 evaluates the electrocardiogram data based on the circumstance data representing the course of events and location of measurement of the electrocardiogram data and on the record data about the body of the person P. For example, the electrocardiogram evaluation apparatus 10 selects an evaluation model corresponding to the physical condition of the person P determined based on the circumstance data and the record data, and evaluates the electrocardiogram data of the person P using the selected evaluation model.

After that, the evaluating unit 14 of the electrocardiogram evaluation apparatus 10 inputs the electrocardiogram data of the target person P into an evaluation model selected in accordance with the determination result as described above, and performs an evaluation based on output data that is output from the evaluation model. For example, as a result of input of the electrocardiogram data into the evaluation model, when output data indicating a specific disease such as myocardial infarction is output, the evaluating unit 14 evaluates that there is a high possibility of the specific disease. Alternatively, the electrocardiogram evaluation apparatus 10 extracts a detection value that can be detected from the waveform of the electrocardiogram data, compares the detection value with a reference value corresponding to the physical condition of the person P determined based on the circumstance data and the record data, and evaluates the presence or absence of a specific disease based on the result.

As described above, according to this example embodiment, the electrocardiogram of a person P is evaluated using an evaluation model or a reference value in accordance with a circumstance in which the electrocardiogram has been measured, for example, the course of events and location that the electrocardiogram has been measured. consequently, it is possible to evaluate electrocardiogram data using criteria suited to the condition of a person P when the electrocardiogram is measured, and it is possible to obtain more accurate evaluation results. As a result, for example, it is possible to obtain electrocardiogram evaluation results that can accurately distinguish between a healthy young person and a patient with acute myocardial infarction, whose electrocardiograms can have similar waveforms, or between patients with different diseases.

Second Example Embodiment

Figure 4:
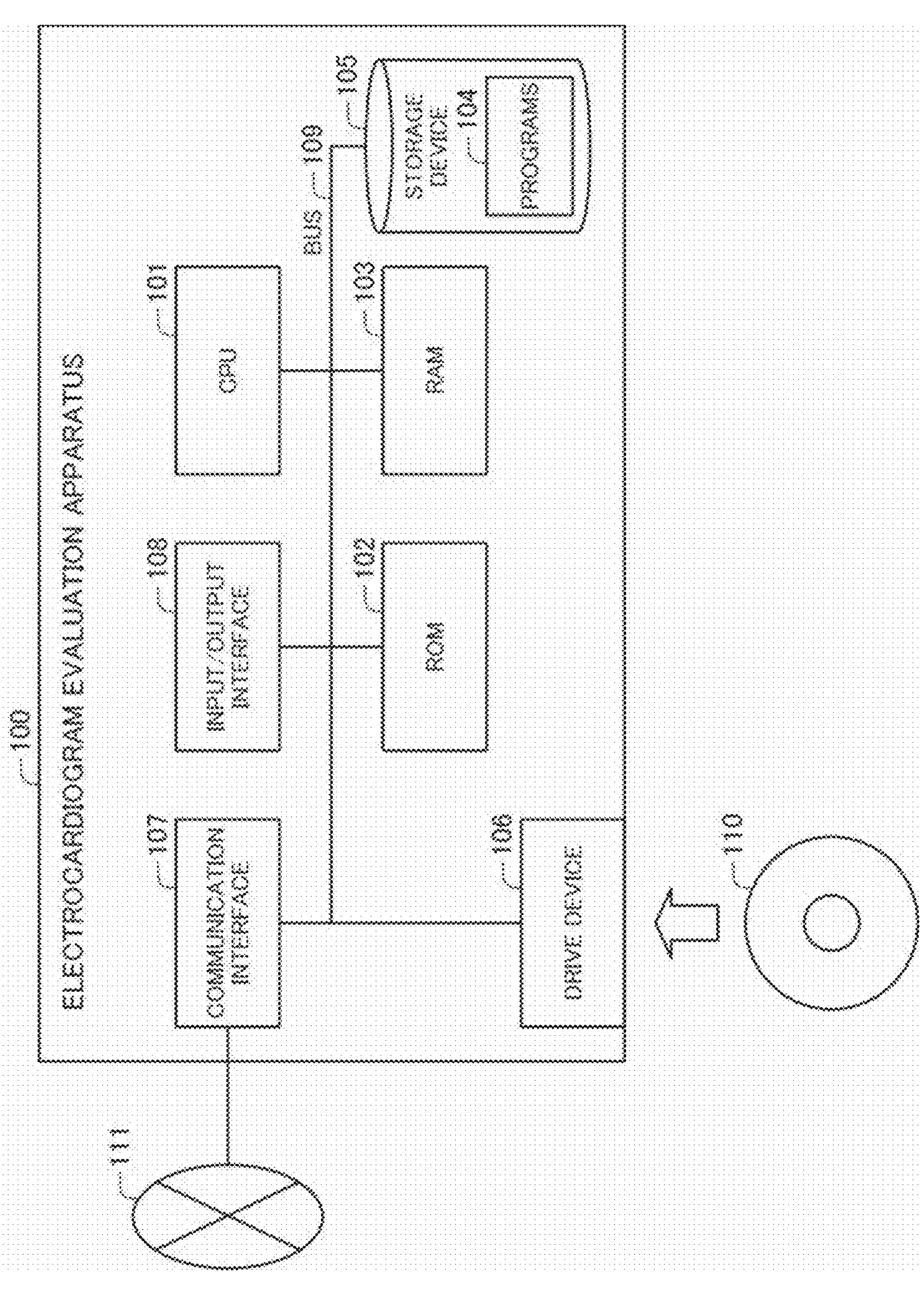
FIG. 4 is a block diagram showing the hardware configuration of an electrocardiogram evaluation apparatus in a second example embodiment of the present invention.
Figure 5:
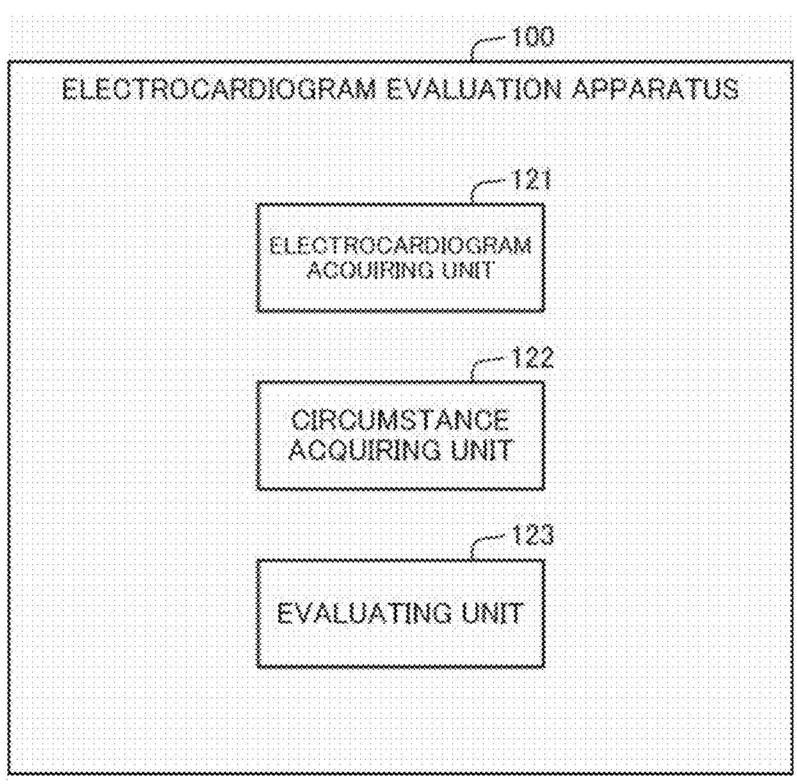
FIG. 5 is a block diagram showing the configuration of the electrocardiogram evaluation apparatus in the second example embodiment of the present invention.
Figure 6:
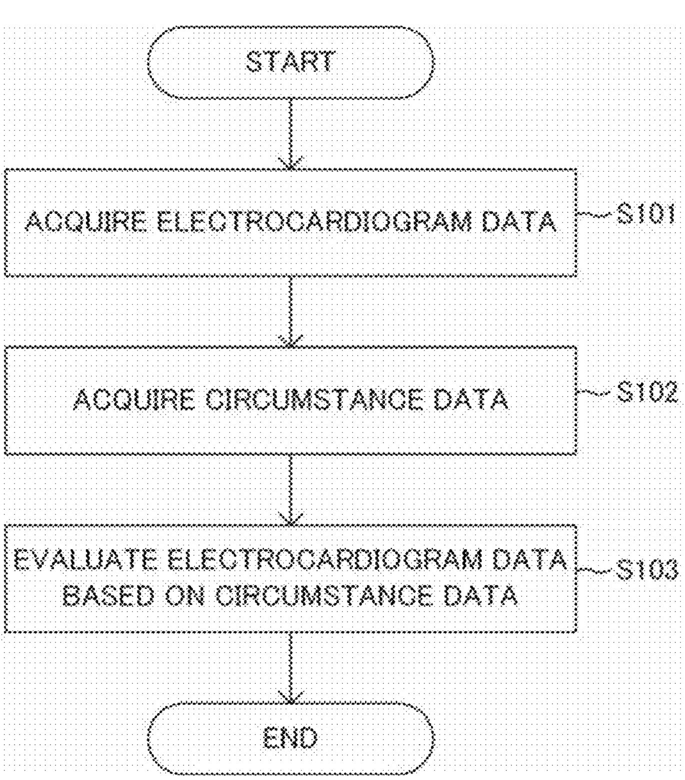
FIG. 6 is a flowchart showing the operation of the electrocardiogram evaluation apparatus in the second example embodiment of the present invention.

Next, a second example embodiment of the present invention will be described with reference to FIGS. 4 to 6. FIGS. 4 and 5 are block diagrams showing the configuration of an electrocardiogram evaluation apparatus in the second example embodiment, and FIG. 6 is a flowchart showing the operation of the electrocardiogram evaluation apparatus. In this example embodiment, the overview of the configurations of the electrocardiogram evaluation apparatus and the electrocardiogram evaluation method described in the above example embodiment is shown.

First, with reference to FIG. 4, the hardware configuration of an electrocardiogram evaluation apparatus 100 in this example embodiment will be described. The electrocardiogram evaluation apparatus 100 is configured with a general information processing apparatus, and as an example, has the following hardware configuration including:

- a CPU (Central Processing Unit) 101 (arithmetic logic unit) (or a GPU (Graphics Processing Unit));
- a ROM (Read Only Memory) 102 (memory unit);
- a RAM (Random Access Memory) 103 (memory unit);
- programs 104 loaded to the RAM 103;
- a storage device 105 storing the programs 104;
- a drive device 106 that reads from and writes into a storage medium 110 outside the information processing apparatus;
- a communication interface 107 connected to a communication network 111 outside the information processing apparatus;
- an input/output interface 108 that inputs and outputs data; and
- a bus 109 that connects the respective components.

Then, the electrocardiogram evaluation apparatus 100 can construct and include an electrocardiogram acquiring unit 121, a circumstance acquiring unit 122, and an evaluating unit 123 shown in FIG. 5 by acquisition and execution of the programs 104 by the CPU 101. The programs 104 are, for example, stored in advance in the storage device 105 or the ROM 102, and are loaded into the RAM 103 and executed by the CPU 101 as necessary. The programs 104 may be provided to the CPU 101 via the communication network 111, or the programs 104 may be stored in the storage medium 110 in advance and read out by the drive device 106 and provided to the CPU 101. However, the electrocardiogram acquiring unit 121, the circumstance acquiring unit 122, and the evaluating unit 123 described above may be constructed using dedicated electronic circuits for realizing such means.

FIG. 4 shows an example of the hardware configuration of the information processing apparatus serving as the electrocardiogram evaluation apparatus 100, and the hardware configuration of the information processing apparatus is not limited to the above case. For example, the information processing apparatus may be configured with part of the above configuration, such as without the drive device 106.

Then, the electrocardiogram evaluation apparatus 100 executes an electrocardiogram evaluation method shown in the flowchart of FIG. 6 by the functions of the electrocardiogram acquiring unit 121, the circumstance acquiring unit 122, and the evaluating unit 123 constructed by the program as described above.

As shown in FIG. 6, the electrocardiogram evaluation apparatus 100 executes processes to:

acquire electrocardiogram data measured from a person (step S101);

acquire circumstance data representing a circumstance in which the electrocardiogram data has been measured (step S102); and evaluate the electrocardiogram data based on the circumstance data (step S103).

Configured as described above, the present invention enables evaluation of electrocardiogram data using criteria suited to circumstances under which the electrocardiogram of a person has been measured, and it is possible to obtain more accurate evaluation results. As a result, for example, it is possible to obtain electrocardiogram evaluation results that can accurately distinguish between a healthy young person and a patient with acute myocardial infarction, whose electrocardiograms may have similar waveforms, or between patients with different diseases.

The abovementioned programs can be stored and provided to a computer using various types of non-transitory computer-readable mediums. Non-transitory computer-readable mediums include various types of tangible storage mediums. Examples of non-transitory computer-readable mediums include a magnetic recording medium (e.g., floppy disk, magnetic tape, hard disk drive), a magneto-optical recording medium (e.g., magneto-optical disk), a CD-ROM (Read Only Memory), a CD-R, a CD-R/W, and a semiconductor memory (e.g., mask ROM, PROM (Programmable ROM), EPROM (Erasable PROM), flash ROM, and RAM (Random Access Memory)). The program may also be provided to a computer by various types of transitory computer-readable mediums. Examples of transitory computer-readable mediums include an electrical signal, an optical signal, and an electromagnetic wave. The temporary computer-readable medium can provide the program to the computer via a wired communication path such as an electric wire or an optical fiber, or via a wireless communication path.

Although the present invention has been described above with reference to the above example embodiments, the present invention is not limited to the above example embodiments. The configuration and details of the present invention can be modified in various ways that are understandable to a person skilled in the art within the scope of the present invention. Moreover, at least one or more of the functions of the electrocardiogram acquiring unit 121, the circumstance acquiring unit 122 and the evaluating unit 123 described above may be executed by an information processing apparatus installed and connected anywhere on the network, that is, may be executed by so-called cloud computing.

Supplementary Notes

The whole or part of the example embodiments disclosed above can be described as the following supplementary notes. The overview of the configurations of an electrocardiogram evaluation method, an electrocardiogram evaluation apparatus, and a program according to the present invention will be described below. However, the present invention is not limited to the following configurations.

Supplementary Note 1

An electrocardiogram evaluation method comprising:

acquiring electrocardiogram data measured from a person;

acquiring circumstance data representing a circumstance in which the electrocardiogram data has been measured; and evaluating the electrocardiogram data based on the circumstance data.

Supplementary Note 2

The electrocardiogram evaluation method according to Supplementary Note 1, comprising acquiring, as the circumstance data, data representing a course of events in which the electrocardiogram data has been measured from the person.

Supplementary Note 3

The electrocardiogram evaluation method according to Supplementary Note 1 or 2, comprising acquiring, as the circumstance data, data representing a location in which the electrocardiogram data has been measured from the person.

Supplementary Note 4

The electrocardiogram evaluation method according to Supplementary Note 3, comprising acquiring the circumstance data based on data representing a sender of the electrocardiogram data.

Supplementary Note 5

The electrocardiogram evaluation method according to any one of Supplementary Notes 1 to 4, comprising acquiring the circumstance data from an electronic medical record of the person.

Supplementary Note 6

The electrocardiogram evaluation method according to any one of Supplementary Notes 1 to 5, comprising:

determining a physical condition of the person in accordance with the circumstance data; and evaluating the electrocardiogram data based on the determined physical condition.

Supplementary Note 7

The electrocardiogram evaluation method according to Supplementary Note 6, comprising determining the physical condition based on record data about a body of the person.

Supplementary Note 8

The electrocardiogram evaluation method according to Supplementary Note 6 or 7, comprising changing a criterion for evaluating the electrocardiogram data in accordance with the determined physical condition.

Supplementary Note 9

The electrocardiogram evaluation method according to any one of Supplementary Notes 6 to 8, comprising selecting a model in accordance with the determined physical condition, and evaluating the electrocardiogram data based on output data that is output by inputting the electrocardiogram data into the selected model.

Supplementary Note 10

The electrocardiogram evaluation method according to any one of Supplementary Notes 1 to 9, comprising selecting a model in accordance with the circumstance data, and evaluating the electrocardiogram data based on output data that is output by inputting the electrocardiogram data into the selected model.

Supplementary Note 11

An electrocardiogram evaluation apparatus comprising:

an electrocardiogram acquiring unit that acquires electrocardiogram data measured from a person;

a circumstance acquiring unit that acquires circumstance data representing a circumstance in which the electrocardiogram data has been measured; and an evaluating unit that evaluates the electrocardiogram data based on the circumstance data.

Supplementary Note 12

The electrocardiogram evaluation apparatus according to Supplementary Note 11, wherein the circumstance acquiring unit acquires, as the circumstance data, data representing a course of events in which the electrocardiogram data has been measured from the person.

Supplementary Note 13

The electrocardiogram evaluation apparatus according to Supplementary Note 11 or 12, wherein the circumstance acquiring unit acquires, as the circumstance data, data representing a location in which the electrocardiogram data has been measured from the person.

Supplementary Note 14

The electrocardiogram evaluation apparatus according to Supplementary Note 13, wherein the circumstance acquiring unit acquires the circumstance data based on data representing a sender of the electrocardiogram data.

Supplementary Note 15

The electrocardiogram evaluation apparatus according to any one of Supplementary Notes 11 to 14, wherein the circumstance acquiring unit acquires the circumstance data from an electronic medical record of the person.

Supplementary Note 16

The electrocardiogram evaluation apparatus according to any one of Supplementary Notes 11 to 15, further comprising a determining unit that determines a physical condition of the person in accordance with the circumstance data, wherein the evaluating unit evaluates the electrocardiogram data based on the determined physical condition.

Supplementary Note 17

The electrocardiogram evaluation apparatus according to Supplementary Note 16, wherein the determining unit determines the physical condition based on record data about a body of the person.

Supplementary Note 18

The electrocardiogram evaluation apparatus according to Supplementary Note 16 or 17, wherein the evaluating unit changes a criterion for evaluating the electrocardiogram data in accordance with the determined physical condition.

Supplementary Note 19

The electrocardiogram evaluation apparatus according to any one of Supplementary Notes 16 to 18, wherein the evaluating unit selects a model in accordance with the determined physical condition, and evaluates the electrocardiogram data based on output data that is output by inputting the electrocardiogram data into the selected model.

Supplementary Note 20

The electrocardiogram evaluation apparatus according to any one of Supplementary Notes 11 to 19, wherein the evaluating unit selects a model in accordance with the circumstance data, and evaluates the electrocardiogram data based on output data that is output by inputting the electrocardiogram data into the selected model.

Supplementary Note 21

A non-transitory computer-readable storage medium storing a program comprising instructions for causing a computer to execute processes to:

acquire electrocardiogram data measured from a person;

acquire circumstance data representing a circumstance in which the electrocardiogram data has been measured; and evaluate the electrocardiogram data based on the circumstance data.

REFERENCE SIGNS LIST

10 electrocardiogram evaluation apparatus
11 electrocardiogram acquiring unit

12 circumstance acquiring unit
13 determining unit
14 evaluating unit
16 evaluation model storing unit
20 electronic medical record apparatus
30 electrocardiogram measurement apparatus
P person
100 electrocardiogram evaluation apparatus
101 CPU
102 ROM
103 RAM
104 programs
105 storage device
106 drive device
107 communication interface
108 input/output interface
109 bus
110 storage medium
111 communication network
121 electrocardiogram acquiring unit
122 circumstance acquiring unit
123 evaluating unit

What is claimed is:

1. An electrocardiogram evaluation method comprising:

acquiring electrocardiogram data measured from a person;

acquiring circumstance data representing a circumstance in which the electrocardiogram data has been measured; and determining a physical condition of the person in accordance with the circumstance data, selecting a model in accordance with the determined physical condition, and evaluating the electrocardiogram data based on output data that is output by inputting the electrocardiogram data into the selected model.

2. The electrocardiogram evaluation method according to claim 1, comprising acquiring, as the circumstance data, data representing a course of events in which the electrocardiogram data has been measured from the person.

3. The electrocardiogram evaluation method according to claim 1, comprising acquiring, as the circumstance data, data representing a location in which the electrocardiogram data has been measured from the person.

4. The electrocardiogram evaluation method according to claim 3, comprising acquiring the circumstance data based on data representing a sender of the electrocardiogram data.

5. The electrocardiogram evaluation method according to claim 1, comprising acquiring the circumstance data from an electronic medical record of the person.

6. The electrocardiogram evaluation method according to claim 1, comprising determining the physical condition based on record data about a body of the person.

7. The electrocardiogram evaluation method according to claim 1, comprising changing a criterion for evaluating the electrocardiogram data in accordance with the determined physical condition.

8. The electrocardiogram evaluation method according to claim 1, comprising selecting the model in accordance with the circumstance data, and evaluating the electrocardiogram data based on output data that is output by inputting the electrocardiogram data into the selected model.

9. An electrocardiogram evaluation apparatus comprising:

at least one memory storing processing instructions; and at least one processor configured to execute the processing instructions to:

acquire electrocardiogram data measured from a person;

acquire circumstance data representing a circumstance in which the electrocardiogram data has been measured; and determine a physical condition of the person in accordance with the circumstance data, select a model in accordance with the determined physical condition, and evaluate the electrocardiogram data based on output data that is output by inputting the electrocardiogram data into the selected model.

10. A non-transitory computer-readable storage medium storing a program comprising instructions for causing a computer to execute processes to:

acquire electrocardiogram data measured from a person;

acquire circumstance data representing a circumstance in which the electrocardiogram data has been measured; and determine a physical condition of the person in accordance with the circumstance data, select a model in accordance with the determined physical condition, and evaluate the electrocardiogram data based on output data that is output by inputting the electrocardiogram data into the selected model.

* * * * *